United States Patent
Seki et al.

(10) Patent No.: US 8,774,491 B2
(45) Date of Patent: Jul. 8, 2014

(54) SUBSTRATE PROCESSING APPARATUS, SUBSTRATE PROCESSING METHOD, AND COMPUTER-READABLE RECORDING MEDIUM HAVING PROGRAM FOR EXECUTING THE SUBSTRATE PROCESSING METHOD RECORDED THEREIN

(75) Inventors: Shinichi Seki, Koshi (JP); Hiroshi Tomita, Koshi (JP); Nobutaka Fukunaga, Koshi (JP); Toshifumi Sohara, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 52 days.

(21) Appl. No.: 13/438,011

(22) Filed: Apr. 3, 2012

(65) Prior Publication Data
US 2012/0257813 A1 Oct. 11, 2012

(30) Foreign Application Priority Data
Apr. 6, 2011 (JP) .................................. 2011-084827

(51) Int. Cl.
*G06K 9/00* (2006.01)
*G01N 21/88* (2006.01)

(52) U.S. Cl.
USPC ........................................................ 382/144

(58) Field of Classification Search
None
See application file for complete search history.

(56) References Cited

U.S. PATENT DOCUMENTS

| 2005/0259235 A1* | 11/2005 | Kurosawa ........................ 355/55 |
| 2007/0200512 A1* | 8/2007 | Gotou et al. .................. 315/309 |
| 2009/0009640 A1* | 1/2009 | Ishii ............................... 348/294 |
| 2009/0062613 A1* | 3/2009 | Mitsuhashi .................... 600/118 |
| 2010/0074515 A1* | 3/2010 | Zhao et al. ..................... 382/149 |

FOREIGN PATENT DOCUMENTS

| JP | 2003-209154 A | 7/2003 |
| JP | 2004-014670 A | 1/2004 |
| JP | 2007-240519 A | 9/2007 |
| JP | 2007-266074 A | 10/2007 |
| JP | 2009-216515 A | 9/2009 |

* cited by examiner

*Primary Examiner* — Atiba O Fitzpatrick
*Assistant Examiner* — Thomas A James
(74) *Attorney, Agent, or Firm* — Abelman, Frayne & Schwab

(57) ABSTRACT

Provided is a substrate processing apparatus that includes: a peripheral exposing unit that performs a peripheral exposing process by irradiating light to a peripheral portion of a substrate while rotating the substrate held by a substrate holding unit using a rotation driving unit; a substrate inspecting unit that performs a substrate inspecting process based on a picked up image of the substrate while moving the substrate using a movement driving unit; and a control unit. The control unit controls the predetermined substrate processing to be stopped when the peripheral exposing process is included in the predetermined substrate processing and an error occurs in the peripheral exposing unit, and controls the substrate inspecting process to be skipped when no error occurs in both of the peripheral exposing unit and a transport unit, the substrate inspecting process is included in the predetermined substrate processing and an error occurs in the substrate inspecting unit.

13 Claims, 11 Drawing Sheets

SUBSTRATE PROCESSING APPARATUS, SUBSTRATE PROCESSING METHOD, AND COMPUTER-READABLE RECORDING MEDIUM HAVING PROGRAM FOR EXECUTING THE SUBSTRATE PROCESSING METHOD RECORDED THEREIN

CROSS-REFERENCE TO RELATED APPLICATIONS

This application is based on and claims priority from Japanese Patent Application No. 2011-084827, filed on Apr. 6, 2011, with the Japanese Patent Office, the disclosure of which is incorporated herein in its entirety by reference.

TECHNICAL FIELD

The present disclosure relates to a substrate processing apparatus, a substrate processing method, and a computer-readable recording medium storing a computer executable program that, when executed, causes a computer to perform the substrate processing method.

BACKGROUND

A photolithography process of a manufacturing process of a semiconductor device includes various processes such as a resist coating process that forms a resist film on the surface of a substrate such as a wafer, an exposing process that irradiates and exposes a pattern formed on the surface of the substrate, and a developing process that develops the substrate after the exposing process. A coating and developing system for performing the respective processes includes a coating device, an exposing device, and a developing device therein, and further, includes a substrate transporting device that transports the substrate among the respective devices.

In the resist coating process, there is a concern that a resist film coated on a peripheral portion of a substrate becomes thick, and as a result, the uniformity of a film thickness of the substrate surface deteriorates or a redundant resist film of the peripheral portion is peeled to generate particles. Therefore, in order to remove the redundant resist film formed at the peripheral portion of the substrate surface, a peripheral exposing process is performed that exposes the peripheral portion of the substrate after the resist coating process. See, for example, Japanese Patent Application Laid-Open No. 2004-14670. Therefore, the coating and developing system includes a peripheral exposing device for performing the peripheral exposing process.

With respect to the substrate after the resist coating process, a substrate inspecting process is performed using a substrate inspecting device to investigate whether a defect such as coating non-uniformity caused by the resist coating process exists on the substrate surface or whether a scratch occurs or a foreign material is attached to the substrate surface. See, for example, Japanese Patent Application Laid-Open No. 2007-240519. For example, an imaging device such as a charge coupled device (CCD) line sensor picks up an image of the substrate by moving relatively with respect to a placing table on which the substrate is disposed and processes the picked up image to determine whether there are defects, scratches, and the attachment of the foreign material. Therefore, the coating and developing system includes a substrate inspecting device having an imaging device and configured to perform a substrate inspecting process.

SUMMARY

An exemplary embodiment of the present disclosure provides a substrate processing apparatus comprising a transport unit including a substrate holding unit that holds a substrate, a rotation driving unit that rotates the substrate holding unit about the center of the substrate holding unit as a rotational axis and a movement driving unit that moves the substrate holding unit horizontally, a peripheral exposing unit including an irradiation unit that irradiates light and configured to perform the peripheral exposing process by irradiating the light to the peripheral portion of the substrate using the irradiation unit while rotating the substrate held by the substrate holding unit using the rotation driving unit, a substrate inspecting unit including an imaging unit that picks up an image and configured to perform the substrate inspecting process that inspects the substrate based on the picked up image while moving the substrate held by the substrate holding unit using the movement driving unit, and a control unit that controls the transport unit, the peripheral exposing unit, and the substrate inspecting unit. The control unit controls the predetermined substrate processing to be stopped when the peripheral exposing process is included in the predetermined substrate processing and an error occurs in the peripheral exposing unit, and the control unit controls the substrate inspecting process to be skipped when no error occurs in both of the peripheral exposing unit and the transport unit, the substrate inspecting process is included in the predetermined substrate processing and an error occurs in the substrate inspecting unit.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
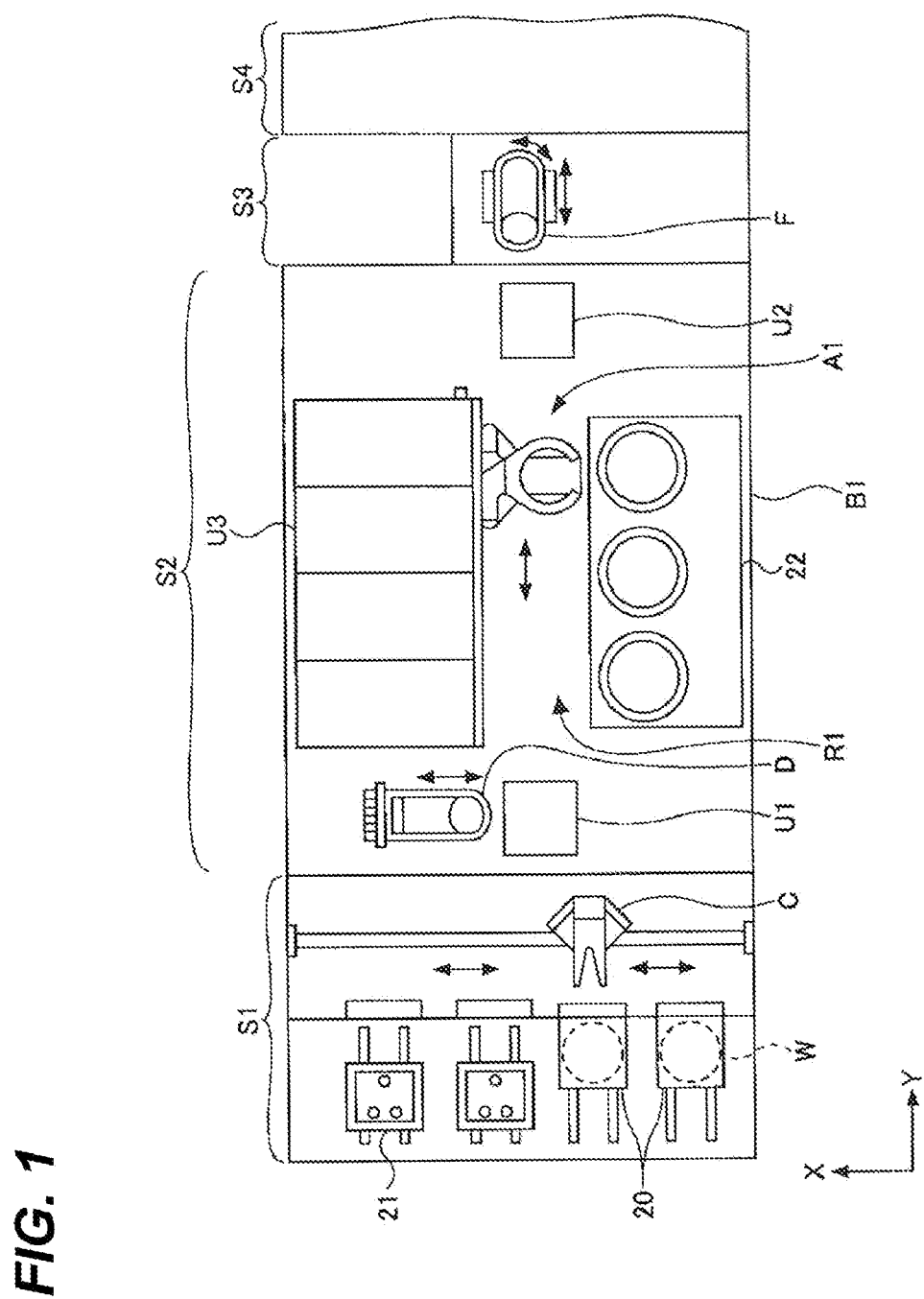
FIG. 1 is a plan view illustrating a configuration of a resist pattern forming apparatus according to an exemplary embodiment of the present disclosure.

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

There are following problems in the coating process and developing process using the peripheral exposing device and the substrate inspecting device.

For example, when the peripheral exposing process and the substrate inspecting process are performed after the resist coating process, a substrate transporting device transports the substrate to the peripheral exposing device to perform the peripheral exposing process after the coating process, and thereafter, the substrate transporting device transports the substrate to the substrate inspecting device to perform the inspecting process after the peripheral exposing process. Therefore, since the substrate transporting device transports the substrate to each of the peripheral exposing device and the substrate inspecting device, the work load of the substrate transporting device increases.

When both of the peripheral exposing device and the substrate inspecting device are installed, an installation area (footprint) of the coating and developing system increases.

Meanwhile, in order to reduce the work load of the substrate transporting device and the installation area of the coating and developing system, the peripheral exposing device and the substrate inspecting device may be integrated in the same substrate processing apparatus. However, when the peripheral exposing process and the substrate inspecting process are performed by the same integrated substrate processing apparatus, the substrate processing apparatus may stop even when an error occurs in a part used only for any one of the peripheral exposing process and the substrate inspecting process.

The present disclosure has been made in an effort to provide a substrate processing apparatus and a substrate processing method capable of reducing the work load of a substrate transporting device, an installation area of an entire processing system, and preventing substrate processing from stopping even when an error occurs in a part used only for any one of a peripheral exposing process and a substrate inspecting process.

In order to solve the problems as described above, the present disclosure considers several measures as described below.

An exemplary embodiment of the present disclosure provides a substrate processing apparatus comprising a transport unit including a substrate holding unit that holds a substrate, a rotation driving unit that rotates the substrate holding unit about the center of the substrate holding unit as a rotational axis, and a movement driving unit that moves the substrate holding unit horizontally, a peripheral exposing unit including an irradiation unit that irradiates light and configured to perform the peripheral exposing process by irradiating the light to the peripheral portion of the substrate using the irradiation unit while rotating the substrate held by the substrate holding unit using the rotation driving unit, a substrate inspecting unit including an imaging unit that picks up an image and configured to perform the substrate inspecting process that inspects the substrate based on the picked up image while moving the substrate held by the substrate holding unit using the movement driving unit, and a control unit that controls the transport unit, the peripheral exposing unit, and the substrate inspecting unit. The control unit controls the predetermined substrate processing to be stopped when the peripheral exposing process is included in the predetermined substrate processing and an error occurs in the peripheral exposing unit, and the control unit controls the substrate inspecting process to be skipped when no error occurs in both of the peripheral exposing unit and the transport unit, the substrate inspecting process is included in the predetermined substrate processing and an error occurs in the substrate inspecting unit.

In the above described substrate processing apparatus, the peripheral exposing unit includes a light emitting unit that emits the light to be irradiated by the irradiation unit, and the control unit controls the predetermined substrate processing to be stopped when the peripheral exposing process is included in the predetermined substrate processing and an error occurs in the light emitting unit.

In the above described substrate processing apparatus, the control unit controls the predetermined substrate processing to be stopped when the peripheral exposing process is included in the predetermined substrate processing and the peripheral exposing unit is in an excessive temperature rise state.

In the above described substrate processing apparatus, the peripheral exposing unit includes a shutter unit that transmits/interrupts the light to be irradiated by the irradiation unit, and the control unit controls the predetermined substrate processing to be stopped when the peripheral exposing process is included in the predetermined substrate processing and an error occurs in the shutter unit.

In the above described substrate processing apparatus, the substrate inspecting unit includes an image processing unit that processes the image picked up by the imaging unit, and the control unit controls the substrate inspecting process to be skipped when no error occurs in both of the peripheral exposing unit and the transport unit, the substrate inspecting process is included in the predetermined substrate processing and a communication error occurs between the imaging unit and the image processing unit.

In the above described substrate processing apparatus, the transport unit includes an alignment unit that aligns a rotation angular position of the substrate held by the substrate holding unit.

Another exemplary embodiment of the present disclosure provides a substrate processing method for performing a predetermined substrate processing comprising at least one of: a peripheral exposing process configured to expose a peripheral portion of a substrate by irradiating light to the peripheral portion of the substrate using an irradiation unit while rotating the substrate held by a substrate holding unit about the center of the substrate holding unit as a rotational axis, and a substrate inspecting process configured to pick up an image of the substrate using an imaging unit of a substrate inspecting unit and inspect the substrate based on the picked up image while moving the substrate held by the substrate holding unit horizontally. The predetermined substrate processing is stopped when the peripheral exposing process is included in the predetermined substrate processing and an error occurs in the peripheral exposing unit, and the substrate inspecting process is skipped when no error occurs in both of the peripheral exposing unit and a transport unit that holds the substrate using the substrate holding unit and rotates and horizontally moves the substrate, the substrate inspecting process is included in the predetermined substrate processing and an error occurs in the substrate inspecting unit.

Yet another exemplary embodiment of the present disclosure provides a computer readable recording medium storing a program, that when executed, causes a computer to perform the substrate processing method as described above.

According to exemplary embodiments of the present disclosure, a load of a substrate transporting device can be reduced, an installation area of an entire processing system can be reduced, and substrate processing can be prevented from stopping even when an error occurs in a part used only for any one of a peripheral exposing process and a substrate inspecting process Hereinafter, a substrate processing apparatus and a substrate processing method according to exemplary embodiments of the present disclosure will be described with a case where the substrate processing apparatus is applied to a coating and developing apparatus.

Referring to FIGS. 1 to 4, a resist pattern forming apparatus in which an exposing device is connected to the coating and developing apparatus will be described with reference to the accompanying drawings.

Figure 2:
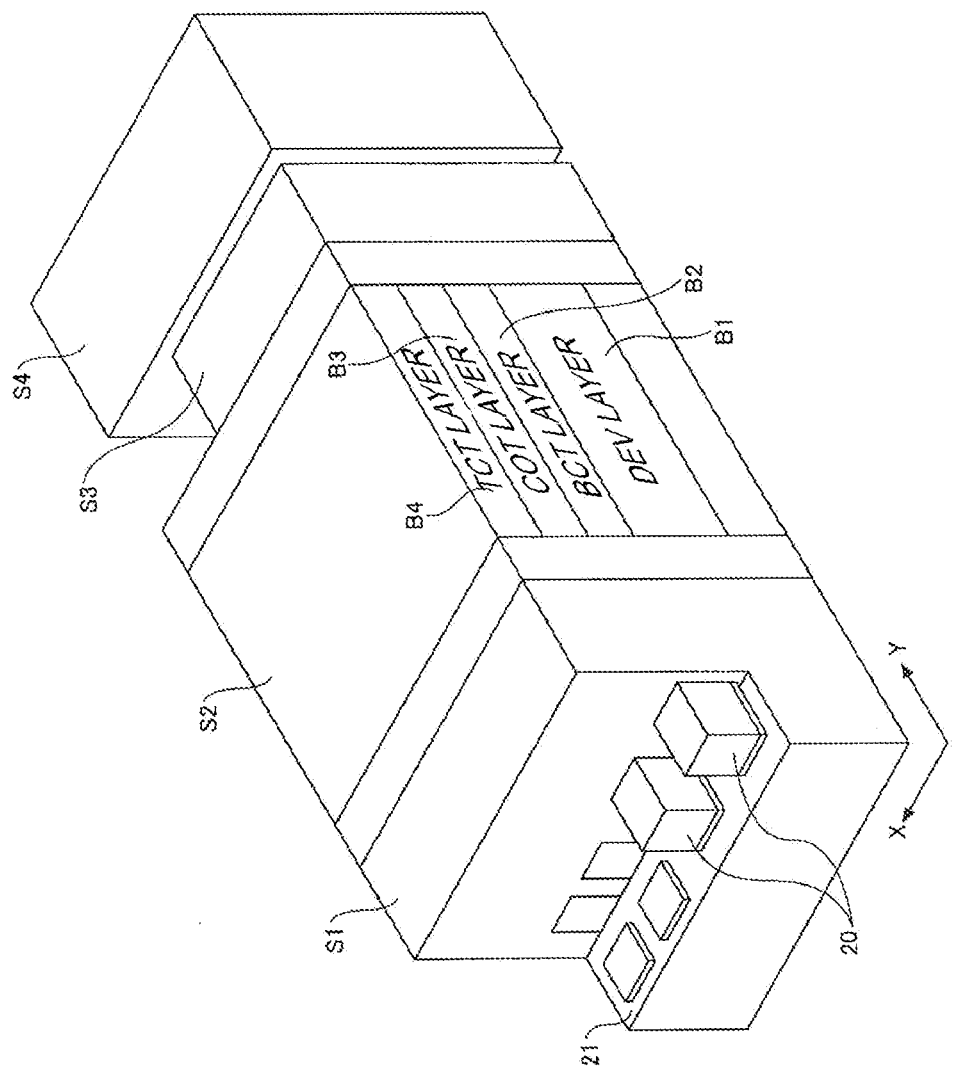
FIG. 2 is a schematic perspective view illustrating the configuration of the resist pattern forming apparatus according to the exemplary embodiment.
Figure 3:
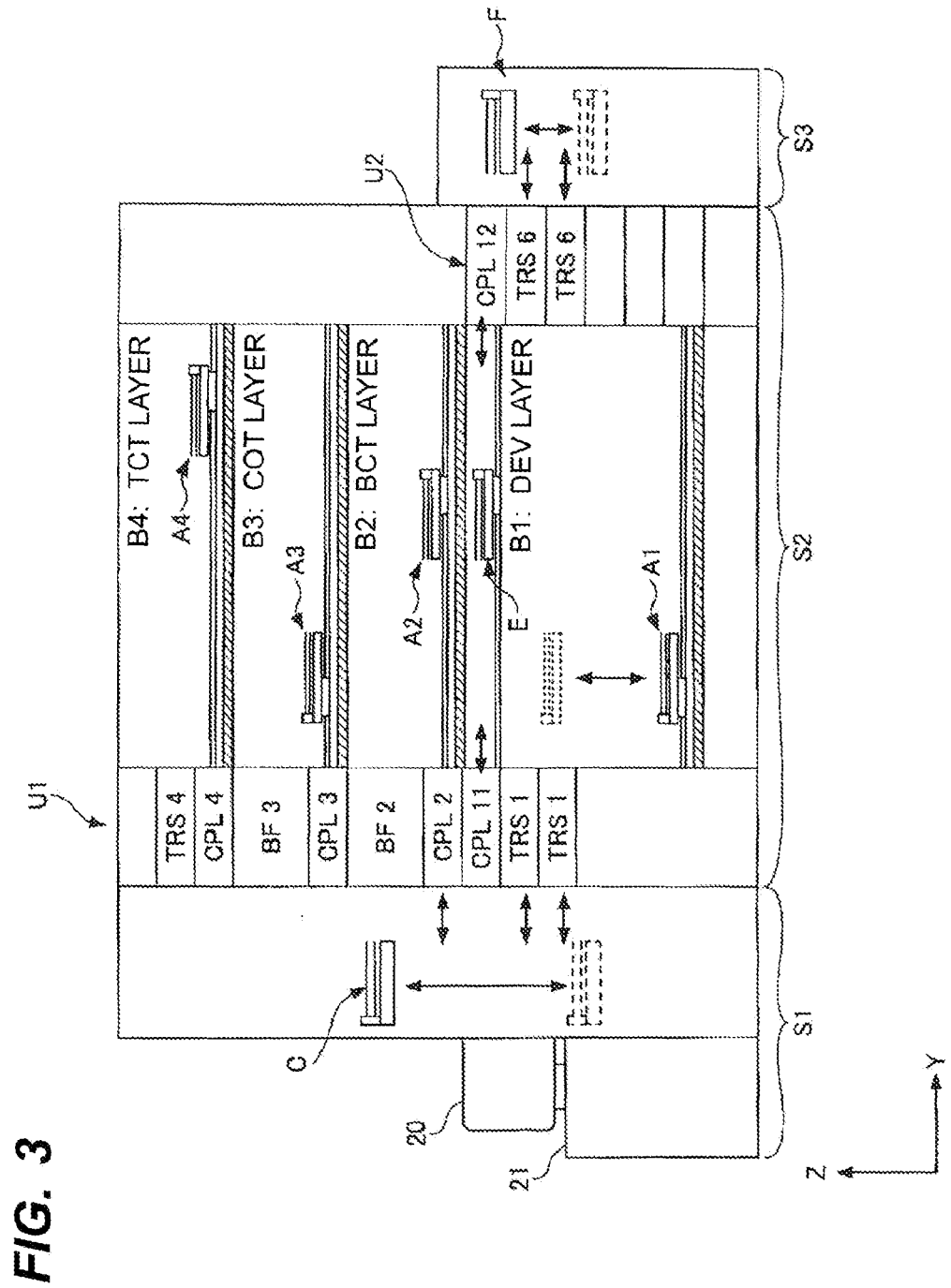
FIG. 3 is a side view illustrating the configuration of the resist pattern forming apparatus according to the exemplary embodiment.
Figure 4:
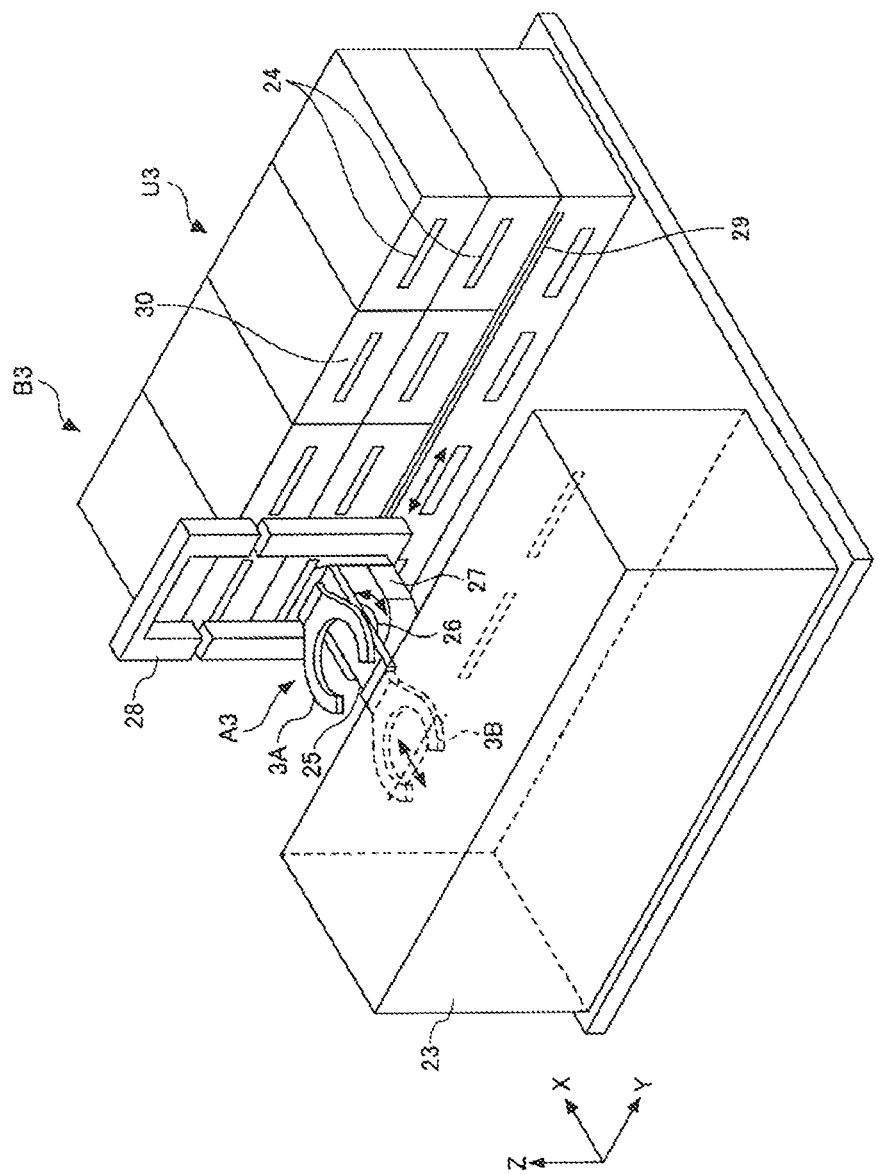
FIG. 4 is a perspective view illustrating a configuration of a third block.

FIG. 1 is a plan view illustrating a configuration of a resist pattern forming apparatus according to the present exemplary embodiment. FIG. 2 is a schematic perspective view illustrating the configuration of the resist pattern forming apparatus according to the present exemplary embodiment. FIG. 3 is a side view illustrating the configuration of the resist pattern forming apparatus according to the present exemplary embodiment. FIG. 4 is a perspective view illustrating a configuration of a third block (COT layer) B3.

The resist pattern forming apparatus includes a carrier block S1, a processing block S2, and an interface block S3 as shown in FIGS. 1 and 2. An exposing device S4 is installed in interface block S3 side of the resist pattern forming apparatus. Processing block S2 is installed to be adjacent to carrier block S1. Interface block S3 is installed to be adjacent to processing block S2 at an opposite side to carrier block S1 of processing block S2. Exposing device S4 is installed to be adjacent to interface block S3 at an opposite side to processing block S2 of interface block S3.

Carrier block S1 includes a carrier 20, a placing table 21, and a carrying member C. Carrier 20 is placed on placing table 21. Carrying member C is used to extract a wafer W from carrier 20, carry wafer W to processing block S2, receive processing-completed wafer W processed in processing block S2, and return wafer W to carrier 20.

Processing block S2, as shown in FIG. 2, includes a rack unit U1, a rack unit U2, a first block (DEV layer) B1, a second block (BCT layer) B2, a third block (COT layer) B3, and a fourth block (TCT layer) B4. First block (DEV layer) B1 is used to perform a developing process. Second block (BCT layer) B2 is used to perform a forming process of an anti-reflection film at a lower layer side of a resist film. Third block (COT layer) B3 is used to perform a coating process of a resist liquid. Fourth block (TCT layer) B4 is used to perform a forming process of the anti-reflection film at an upper layer side of the resist film.

Rack unit U1 is constituted by stacking various modules including transfer modules TRS1, TRS1, CPL11, CPL2, BF2, CPL3, BF3, CPL4, and TRS4 stacked, for example, in sequence from the bottom, as shown in FIG. 3. As shown in FIG. 1, a delivery arm D which is capable of ascending/descending is installed around rack unit U1. Wafer W is transported among the respective processing modules of rack unit U1 by delivery arm D.

Rack unit U2 is constituted by stacking various processing modules including transfer modules TRS6, TRS6, and CPL12 stacked, for example, in sequence from the bottom, as shown in FIG. 3.

In FIG. 3, the transfer module to which the CPL is added also serve as a temperature control cooling module and the transfer module to which the BF is added also serves as a buffer module in which a plurality of sheets of wafers W may be placed.

First block (DEV layer) B1 includes a developing module 22, a transport arm A1, and a shuttle arm E, as shown in FIGS. 1 and 3. Developing module 22 is stacked in two stages vertically in a single first block (DEV layer) B1. Transport arm A1 is used to transport wafer W to two-stage developing module 22. That is, transport arm A1 is a common transport arm that transports wafer W to two-stage developing module 22. Shuttle arm E is used to transport wafer W directly to transfer module CPL12 of rack unit U2 from transfer module CPL11 of rack unit U1.

Second block (BCT layer) B2, third block (COT layer) B3, and fourth block (TCT layer) B4 each include a coating module, a processing module group of a heating and cooling system, and transport arms A2, A3, and A4. The processing module group is used to perform a pre-processing and a post-processing of processing performed in the coating module. Transport arms A2, A3, and A4 are installed between the coating module and the processing module group to transfer wafer W between the coating module and each processing module of the processing module group.

Each of second block (BCT layer) B2 to fourth block (TCT layer) B4 have the same configuration except that the chemical liquid in second block (BCT layer) B2 and fourth block (TCT layer) B4 is for the anti-reflection film and the chemical liquid in third block (COT layer) B3 is a resist liquid.

Herein, referring to FIG. 4, the configuration of third block (COT layer) B3 will be described, which represents second block (BCT layer) B2, third block (COT layer) B3, and fourth block (TCT layer) B4.

Third block (COT layer) B3 includes a coating module 23, a rack unit U3, and transport arm A3. Rack unit U3 includes a plurality of processing modules stacked to constitute a heat processing module group including a heating module and a cooling module. Rack unit U3 is arranged to be opposite to coating module 23. A substrate processing apparatus 30 to be described below is installed to be adjacent to any one of the plurality of processing modules in rack unit U3.

Transport arm A3 is installed between coating module 23 and rack unit U3. In FIG. 4, reference numeral 24 represents a transport hole for delivering wafer W between each processing module and transport arm A3.

Transport arm A3 includes two forks 3 (3A and 3B), a base 25, a rotating mechanism 26, and a lifting table 27.

Two forks 3A and 3B are installed to be vertically overlapped with each other. Base 25 is installed rotatably around a vertical shaft by rotating mechanism 26. Forks 3A and 3B are installed to advance to and retreat from a placing table 33 of substrate processing apparatus 30 to be described below from base 25 by an advance and retreat mechanism (not shown).

Lifting table 27 is installed below rotating mechanism 26 as shown in FIG. 4. Lifting table 27 is installed to be ascended/descended by a lifting mechanism along a Z-axis guide rail (not shown) that extends linearly in the vertical direction (Z-axis direction in FIG. 4). As the lifting mechanism, a known constitution such as a ball screw mechanism or a mechanism using a timing belt may be used. In this example, each of the Z-axis guide rail and the lifting mechanism is covered by a cover body 28 and for example, integrally joined with cover body 28 at an upper side thereof. Cover body 28 is configured to slide along a Y-axis guide rail 29 that extends linearly in a Y-axis direction.

Interface block S3 includes an interface arm F, as shown in FIG. 1. Interface arm F is installed around rack unit U2 of processing block S2. Wafer W is transported between each processing module of rack unit U2 and exposing device S4 by interface arm F.

Wafer W from carrier block S1 is sequentially transported to one transfer module of rack unit U1, for example, transfer module CPL2 corresponding to second block (BCT layer) B2 by carrying member C. Wafer W transported to transfer module CPL2 is transferred to transport arm A2 of second block (BCT layer) B2, transported to each processing module (the coating module and each processing module of the processing module group of the heating and cooling system) through transport arm A2, and processed by each processing module. Therefore, the anti-reflection film is formed on wafer W.

Wafer W having the anti-reflection film is transferred to transport arm A3 of third block (COT layer) B3 through transport arm A2, transfer module BF2 of rack unit U1, delivery arm D, and transfer module CPL3 of rack unit U1. Wafer W is transported to each processing module (the coating module and each processing module of the processing module group of the heating and cooling system) through transport arm A3 and processed by each processing module. Therefore, the resist film is formed on wafer W.

Wafer W having the resist film is transferred to transfer module BF3 of rack unit U1 through transport arm A3.

Wafer W having the resist film is transported to substrate processing apparatus 30 and then peripheral exposing process may be performed by exposing a peripheral portion of wafer W using a peripheral exposing unit 50 or substrate inspecting process may be performed by picking up an image of the surface of wafer W using a substrate inspecting unit 70, as described below.

An anti-reflection film may be further formed on wafer W having the resist film in fourth block (TCT layer) B4. In this case, wafer W is transferred to transport arm A4 of fourth block (TCT layer) B4 through transfer module CPL4, transported to each processing module (the coating module and each processing module of the processing module group of the heating and cooling system) through transport arm A4, and processed by each processing module. Therefore, the anti-reflection film is formed on wafer W. Wafer W having the anti-reflection film is transferred to transfer module TRS4 of rack unit U1 through transport arm A4.

Wafer W having the resist film or wafer W having the anti-reflection film on the resist film is transferred to transfer module CPL11 through delivery arm D and transfer modules BF3 and TRS4. Wafer W transferred to transfer module CPL11 is transported directly to transfer module CPL12 of rack unit U2 by shuttle arm E and thereafter, transferred to interface arm F of interface block S3.

Wafer W transferred to interface arm F is transported to exposing device S4 to be subjected to a predetermined exposing process. Wafer W which has performed the predetermined exposing process is placed in transfer module TRS6 of rack unit U2 and returned to processing block S2, through interface arm F. Wafer W returned to processing block S2 is subjected to developing process in first block (DEV layer) B1. Developed wafer W is returned to carrier 20 through transport arm A1, any one transfer module in rack unit U1, and carrying member C.

Figure 5:
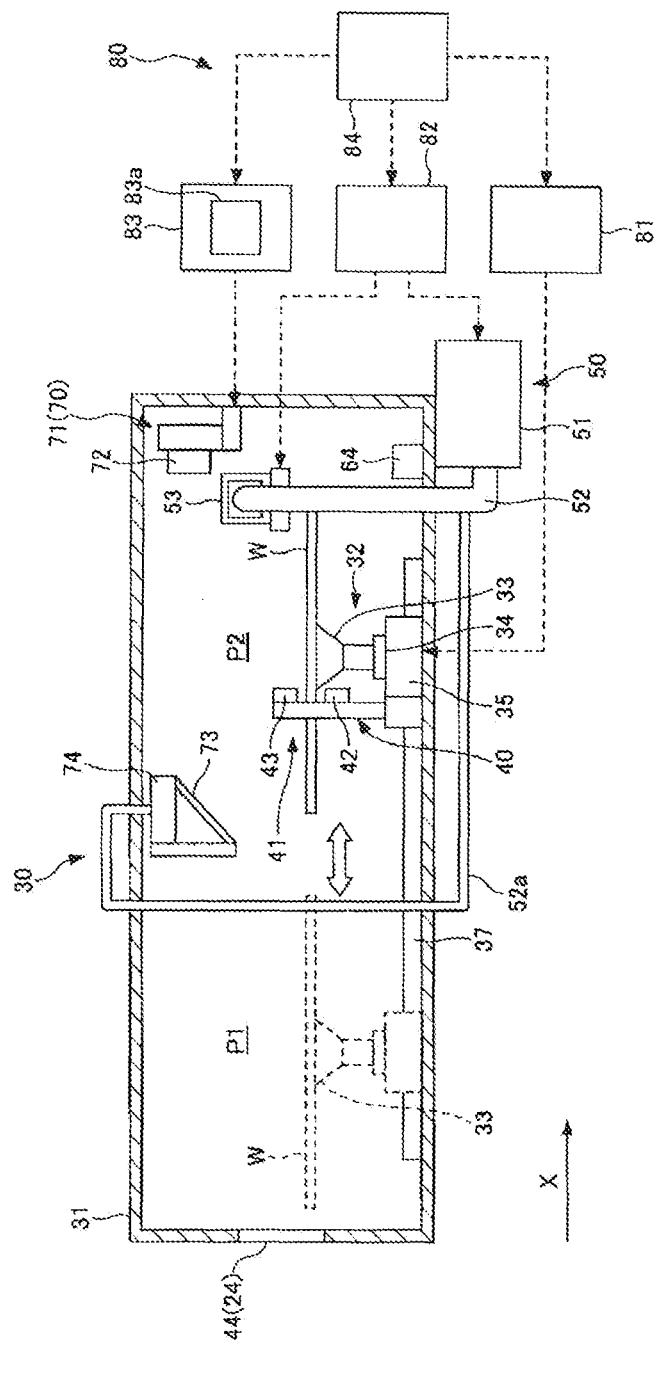
FIG. 5 is a side view including a partial cross section of a substrate processing apparatus.
Figure 6:
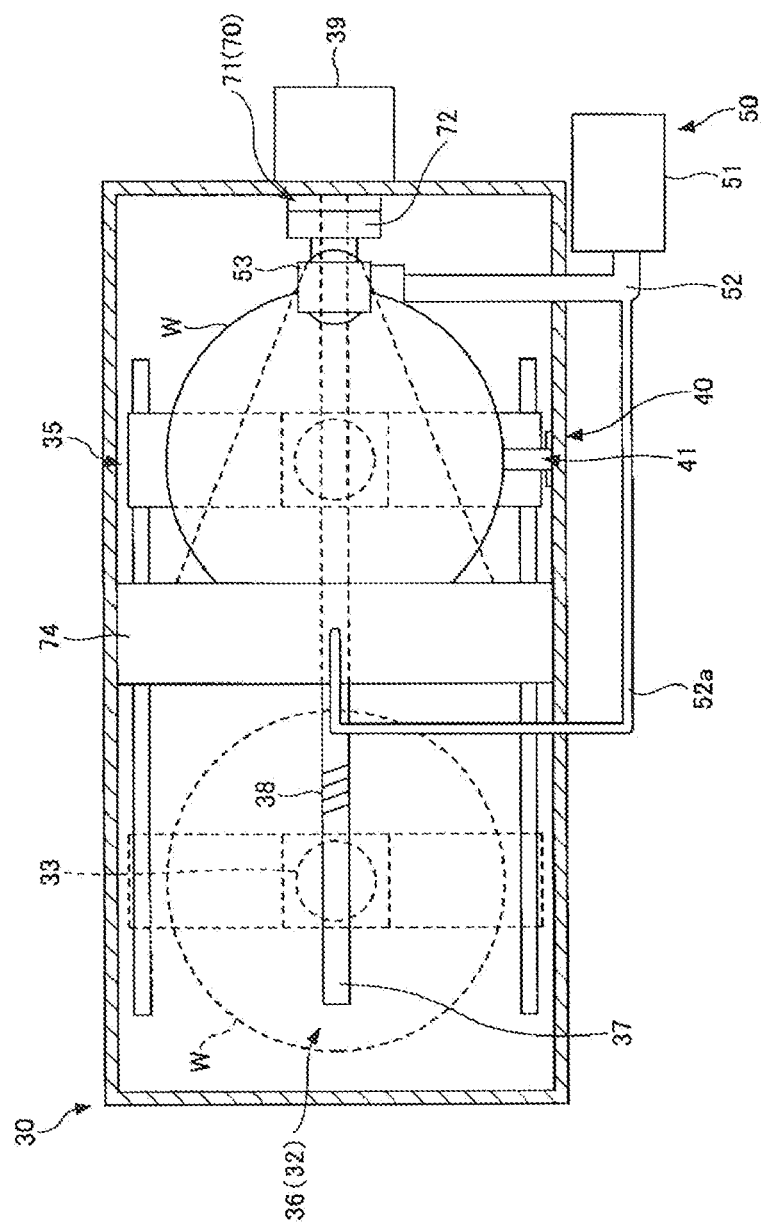
FIG. 6 is a plan view including the partial cross section of the substrate processing apparatus.
Figure 7:
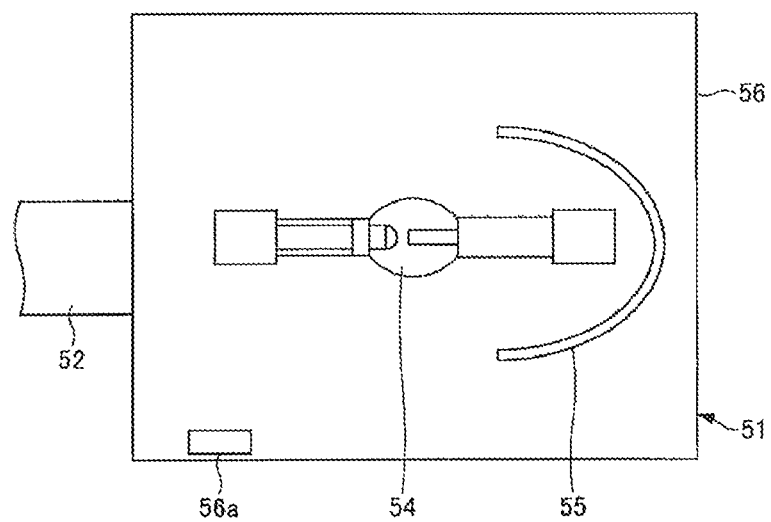
FIG. 7 is a longitudinal cross-sectional view illustrating a configuration of a light emitting unit.
Figure 8A:
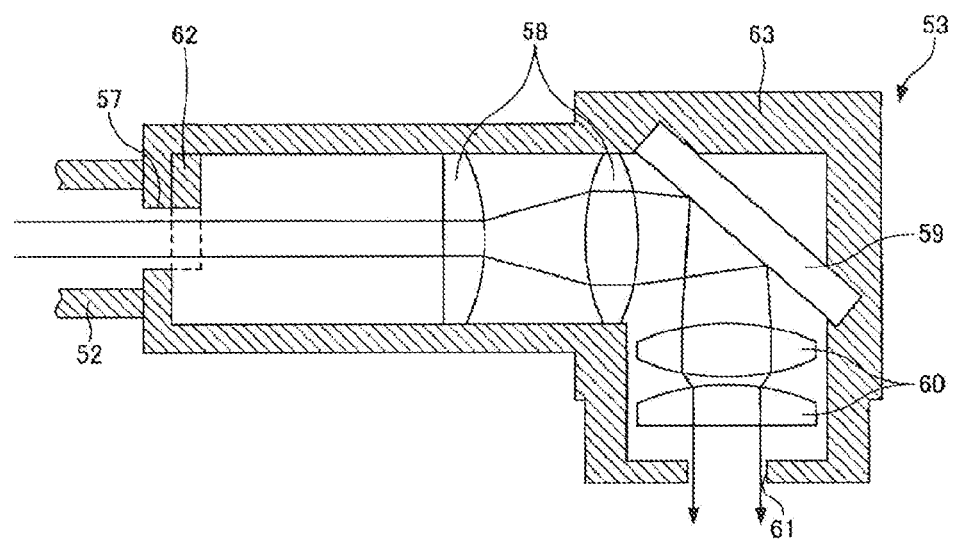
FIGS. 8A and 8B are a longitudinal cross-sectional view and a bottom view, respectively, each illustrating a configuration of an irradiation unit.
Figure 8B:
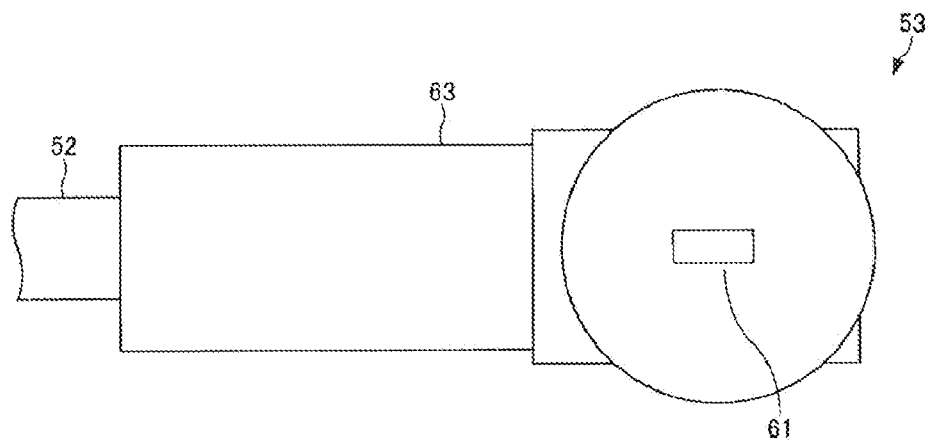
Figure 9A:
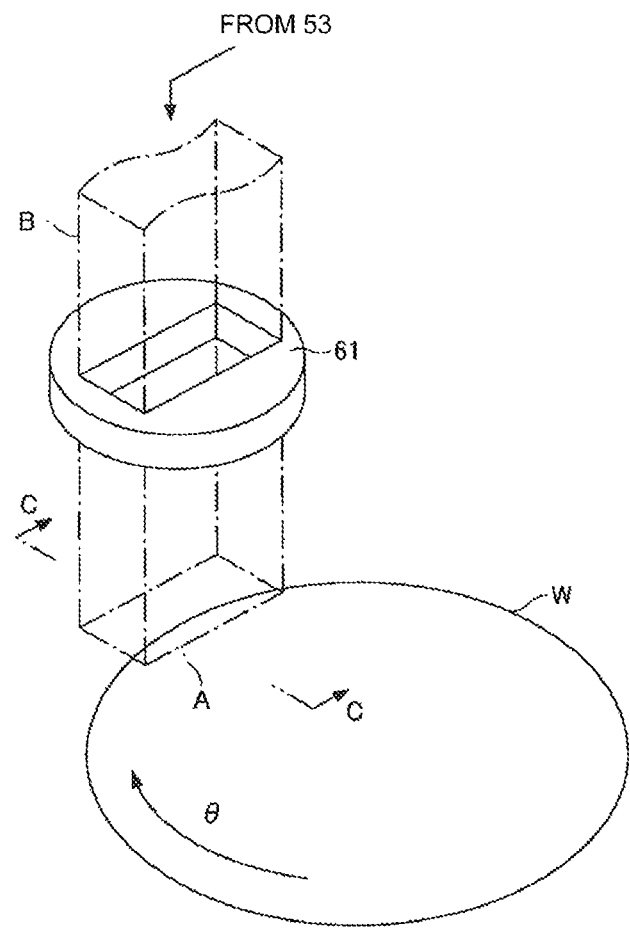
FIGS. 9A and 9B are perspective view and a cross-sectional view, respectively, each illustrating a state where a wafer is peripherally exposed by a peripheral exposing unit.
Figure 9B:
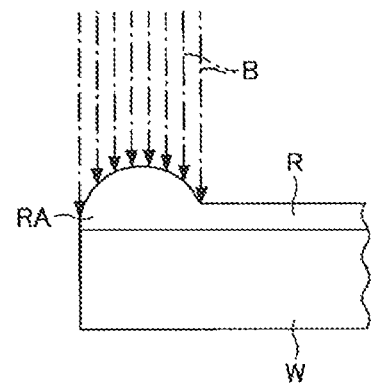

Next, referring to FIGS. 5 to 9, substrate processing apparatus 30 embedded in the resist pattern forming apparatus, and configured to perform the peripheral exposing process and the substrate inspecting process, will be described. FIG. 5 is a side view including a partial cross section of substrate processing apparatus 30. FIG. 6 is a plan view including a partial cross section of substrate processing apparatus 30. FIG. 7 is a longitudinal cross-sectional view illustrating a configuration of a light emitting unit 51. FIG. 8 is a longitudinal cross-sectional view and a bottom view illustrating a configuration of an irradiation unit 53. FIG. 8A illustrates the longitudinal cross-sectional view and FIG. 8B illustrates the bottom view. FIG. 9A is a perspective view illustrating a state where wafer W is peripherally exposed by peripheral exposing unit 50. FIG. 9B is a cross-sectional view taken along line C-C of FIG. 9A.

Substrate processing apparatus 30 is used to expose wafer W, which is for example, processed in each module of third block (COT layer) B3 to have the resist film, by exposing the peripheral portion of wafer W and perform the substrate inspecting process of wafer W by picking up an image of the surface of wafer W, as described above. Substrate processing apparatus 30 may be installed at any one place in the resist pattern forming apparatus, and as described above, may be installed adjacent to each processing module in, for example, third block (COT layer) B3.

Substrate processing apparatus 30 includes a casing 31, a transport unit 32, peripheral exposing unit 50, and substrate inspecting unit 70.

Transport unit 32 includes placing table 33, a rotation driving unit 34, a movement driving unit 35, and an alignment unit 40.

Placing table 33 is used to hold disposed wafer W and installed in a lower space within casing 31 covering an outer surface of the substrate processing apparatus. Placing table 33 includes for example, a vacuum chuck. Placing table 33 is rotatably installed and rotated by rotation driving unit 34 such as a motor.

Movement driving unit 35 includes a ball screw mechanism 36 and a guide rail 37.

Ball screw mechanism 36 and guide rail 37 are installed on the bottom side of casing 31 to extend from one end (a left side of FIG. 5) to the other end (a right side of FIG. 5) of casing 31. Ball screw mechanism 36 includes a screw shaft 38 joining (screw-joining) with placing table 33 movably in an X direction and a motor 39 rotating screw shaft 38 forwardly and reversely. Guide rail 37 is installed in parallel with screw shaft 38 with a pair so as to slidably support placing table 33. That is, placing table 33 is installed movably in the X direction along ball screw mechanism 36 and guide rail 37. Placing table 33 and rotation driving unit 34 are driven to move in the ±X direction along guide rail 37 by motor 39.

Herein, a case where movement driving unit 35 includes ball screw mechanism 36 is described, but movement driving unit 35 does not particularly need to include ball screw mechanism 36 and may include, for example, a cylinder mechanism or a belt mechanism.

Alignment unit 40 includes a sensor unit 41 and rotation driving unit 34 as described above.

Sensor unit 41 is used to detect the position of a notch portion (cutout portion) of wafer W on placing table 33. Sensor unit 41 includes for example, a light emitting element 42 and a light receiving element 43 that make a pair. Sensor unit 41 is installed such that the peripheral portion of wafer W is vertically interposed between light emitting element 42 and light receiving element 43 when wafer W disposed and held on placing table 33 is placed at an alignment position P2 which is one end side of casing 31. Based on a detection result of the position of the notch portion by sensor unit 41, placing table 33 may be rotated by rotation driving unit 34 to align an angle of wafer W.

A transport hole 44 (the same as reference numeral 24 in FIG. 4) through which transport arm A3 carries in/out wafer W by driving forks 3A and 3B to advance to and retreat from placing table 33 is formed at an end in casing 31.

Peripheral exposing unit 50 includes light emitting unit 51, a light guiding member 52, and irradiating unit 53.

As shown in FIG. 7, light emitting unit 51 includes a light source 54, a light focusing mirror 55, and a light source box 56. Light source 54 emits light that exposes wafer W disposed and held on placing table 33. As for light source 54, for example, an extra-high pressure mercury lamp may be used. Light focusing mirror 55 focuses the light from light source 54. Light source box 56 receives light source 54 and light focusing mirror 55. As shown in FIG. 5, light emitting unit 51 may be installed below casing 31.

Irradiating unit 53 corresponds to an irradiator and light source 54 corresponds to the light emitting unit in the present disclosure.

Light emitting unit 51 may have a temperature fuse 56a installed within light source box 56 or around light source box 56. Therefore, when an error occurs in light emitting unit 51 to be in an excessive temperature rise state, the state may be detected by temperature fuse 56a.

Light guiding member 52 is installed to connect light emitting unit 51 and irradiating unit 53. Light guiding member 52 includes, for example, an optical fiber having a core material transparent to light, such as quartz and guides the light emitted from light source 54 to irradiating unit 53 from light emitting unit 51.

As shown in FIGS. 8A and 8B, irradiating unit 53 includes an incidence-side slit 57, an incidence-side lens 58, a mirror 59, an emission-side lens 60, an emission-side slit 61, a shutter 62, and a cylindrical cover body 63. Cylindrical cover body 63 receives incidence-side slit 57, incidence-side lens 58, mirror 59, emission-side lens 60, and emission-side slit 61. Incidence-side slit 57 has for example, a rectangular shape and forms a cross-sectional shape of light flux when light guided by passing light guiding member 52 is incident in the irradiating unit 53. The shape of the light flux and the direction of the light incident in irradiating unit 53 through incidence-side slit 57 are changed through incidence-side lens 58, mirror 59, and emission-side lens 60, such that the light is guided to emission-side slit 61. Emission-side slit 61 has for example, the rectangular shape and forms the cross-sectional shape of light flux when light passing emission-side lens 60 is emitted from irradiating unit 53.

Shutter 62 corresponds to a shutter unit in the present disclosure.

The size of incidence-side slit 57 may be for example, 4 mm×10 mm when incidence-side slit 57 has the rectangular shape. The size of emission-side slit 61 may be for example, 4 mm×10 mm when emission-side slit 61 has the rectangular shape.

Shutter 62 is used to control transmission/interruption of the light in irradiating unit 53 by opening/closing shutter 62.

Peripheral exposing unit 50 may have a light amount sensor 64 including, for example, a photodiode. Light amount sensor 64 is installed at an emission side of irradiating unit 53 and measures the amount of the light emitted from irradiating unit 53. Therefore, it may be determined whether the amount of light emitted from irradiating unit 53 by opening/closing shutter 62 is within a predetermined range.

According to peripheral exposing unit 50, light B from light source 54 is emitted from emission-side slit 61 formed in irradiating unit 53 to be evenly irradiated to a predetermined area A of the peripheral portion of the surface of wafer W having a resist film R, as shown in FIG. 9A. In this state, wafer W may be rotated by rotation driving unit 34 and the peripheral portion of the surface of wafer W having a redundant resist film RA is irradiated (exposed) to light B, as shown in FIG. 9B.

Substrate inspecting unit 70 includes an imaging unit 71 and an image processing unit 83a. Image processing unit 83a is installed in a third control device 83 to be described below.

Imaging unit 71 is installed in an upper space of casing 31 covering the outer surface of the substrate processing apparatus. Imaging unit 71 includes an imaging device 72, a half mirror 73, and a lighting device 74. Imaging device 72 is fixed to one end (a right side of FIG. 5) of casing 31. In the present exemplary embodiment, a wide-angle type CCD camera is used as imaging device 72. Half mirror 73 and lighting device 74 are fixed to the vicinity of the center in an X direction of casing 31. Lighting device 74 is installed in the rear side of half mirror 73. Light from lighting device 74 passes through half mirror 73 to be irradiated downwardly from half mirror 73. Reflection light of an object in the irradiation area is reflected by half mirror 73 to be absorbed in imaging device 72. That is, imaging device 72 may pick up the object in the irradiation area.

According to imaging unit 71, while placing table 33 moves in the X direction (alternatively, −X direction) along guide rail 37 in the lower space in casing 31, imaging unit 71 fixed to the upper space in casing 31 scans a top surface of wafer W on placing table 33. Therefore, the entire top surface of wafer W may be picked up.

As shown in FIGS. 5 and 6, in lighting device 74, a light guiding member 52a is branched from light guiding member 52 of peripheral exposing unit 50, and as a result, lighting device 74 may use the light from light source 54 of peripheral exposing unit 50. Therefore, the light source may be commonly used between peripheral exposing unit 50 and substrate inspecting unit 70 and the number of light sources installed in substrate processing apparatus 30 may be reduced.

According to the present exemplary embodiment, the peripheral exposing device and the substrate inspecting device may be integrated as the same substrate processing apparatus. Accordingly, the work load of the substrate transporting device that transports the wafer during the peripheral exposing process and the substrate inspecting process may be reduced and the installation area (footprint) of the entire processing system is also reduced.

Next, referring to FIGS. 5 and 10, a control unit 80 of substrate processing apparatus 30 will be described.

Figure 10:
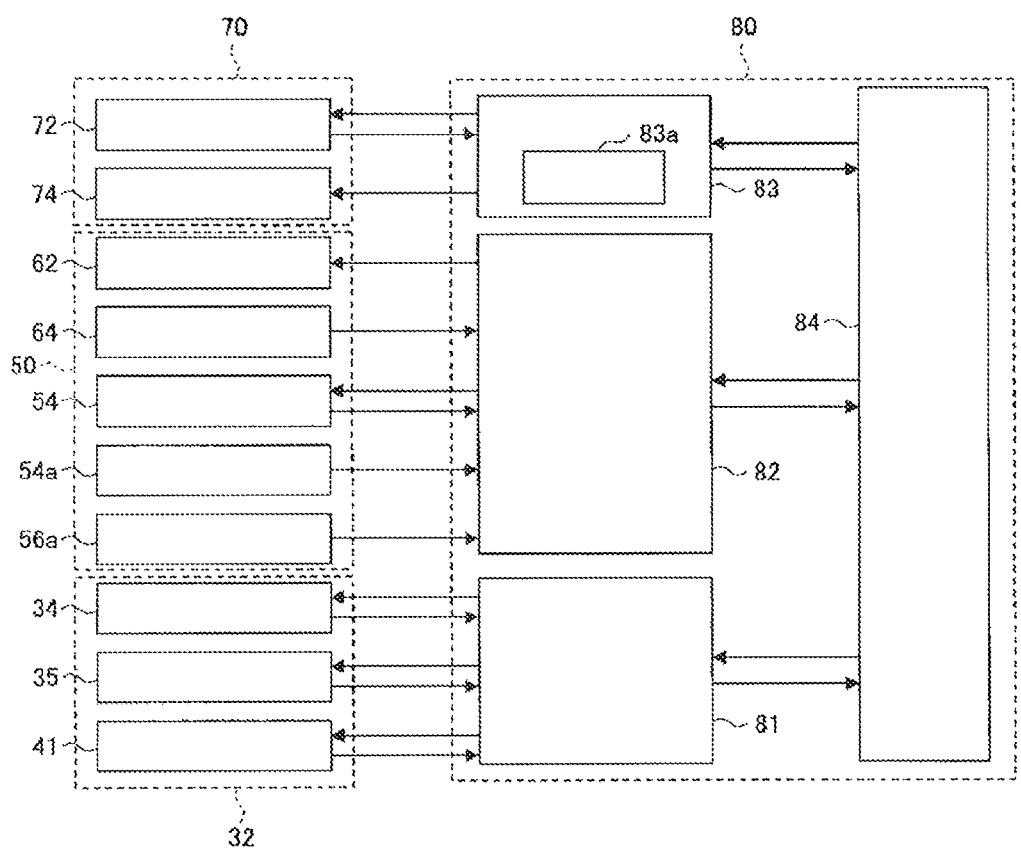
FIG. 10 is a diagram illustrating a configuration of a control unit of the substrate processing apparatus.

FIG. 10 is a diagram illustrating a configuration of control unit 80 of substrate processing apparatus 30.

Control unit 80 includes a first control device 81, a second control device 82, a third control device 83, and a main body control device 84.

First control device 81 controls the rotation and movement of wafer W by transport unit 32 and alignment by alignment unit 40. Second control device 82 controls peripheral exposing process of wafer W performed by peripheral exposing unit 50. Third control device 83 includes an image processing unit 83a and controls the image picking up of wafer W performed by imaging device 72 of substrate inspecting unit 70 and processing of the picked up image using image processing unit 83a. Main body control device 84 controls first to third control devices 81 to 83.

First control device 81 controls the driving of rotation driving unit 34 included in transport unit 32, for example, ON, OFF, and a rotating speed. That is, the driving, stop, and furthermore, a driving speed of rotation driving unit 34 are controlled according to a driving signal outputted to rotation driving unit 34 from first control device 81. An encoder signal at that time is outputted to first control device 81 from rotation driving unit 34 driven by the driving signal.

First control device 81 controls the driving of movement driving unit 35 included in transport unit 32, for example, ON, OFF, and the rotating speed of motor 39. That is, the driving, stop, and furthermore, the driving speed of motor 39 are controlled according to a driving signal outputted to motor 39 of movement driving unit 35 from first control device 81. An encoder signal at that time is outputted to first control device 81 from motor 39 driven by the driving signal.

First control device 81 controls driving of sensor unit 41 included in alignment unit 40, for example, ON and OFF of light emitting element 42 and ON and OFF of light receiving element 43. That is, electrical conduction, stop, and furthermore, conduction current of light emitting element 42 are controlled according to a signal outputted to light emitting element 42 from first control device 81. Electrical conduction, stop, and furthermore, conduction current of light receiving element 43 are controlled according to a signal outputted to light receiving element 43 from first control device 81. A signal corresponding to the amount of light received by light receiving element 43 is outputted to first control device 81 from light receiving element 43.

Second control device 82 controls driving of light source 54 included in peripheral exposing unit 50, for example, ON and OFF of light source 54. That is, electrical conduction, stop, and furthermore, conduction current of light source 54 are controlled according to a driving signal outputted to light source 54 from second control device 82. A signal corresponding to an emission state of light source 54 is outputted to second control device 82 from an electrical circuit 54a of light source 54. A signal corresponding to whether an excessive temperature rise occurs around of light source 54 is outputted to second control device 82 from the temperature fuse 56a installed inside or around light source 54.

Second control device 82 controls the emission or interruption of light for exposing process using shutter 62 included in peripheral exposing unit 50. That is, an opening/closing operation of shutter 62 is controlled according to a driving signal outputted to shutter 62 from second control device 82. A signal indicating the opening/closing state of shutter 62 is outputted to second control device 82 from light amount sensor 64 installed around irradiating unit 53 depending on whether or not the light is irradiated from irradiating unit 53.

Third control device 83 controls imaging using imaging device 72 included in substrate inspecting unit 70 and irradiation or stop of light by lighting device 74 (alternatively, transmission or interruption of light from the lighting device by a shutter mechanism (not shown)). That is, imaging, an imaging timing, and an image acquiring time by imaging device 72 are controlled according to an external synchronization signal outputted to imaging device 72 from third control device 83. ON, OFF, and conduction current of lighting device 74 are controlled according to a signal outputted to lighting device 74 from third control device 83. The picked up image is outputted to third control device 83, and image processing process and substrate inspecting process are performed by image processing unit 83a included in third control device 83.

Main body control device 84, which is a super ordinate control device of first control device 81, second control device 82, and third control device 83, and controls the entire resist pattern forming apparatus including first control device 81, second control device 82 and third control device 83.

For example, first control device 81 outputs a predetermined driving signal to rotation driving unit 34, based on a driving signal outputted to first control device 81 from main body control device 84. Meanwhile, main body control device 84 outputs a driving signal even to second control device 82 at the same timing as the driving signal outputted to first control device 81, and second control device 82 outputs, to shutter 62, a predetermined driving signal for opening shutter 62 based on the driving signal. Therefore, the peripheral portion of wafer W may be exposed.

For example, first control device 81 outputs a predetermined driving signal to motor 39, based on the driving signal outputted to first control device 81 from main body control device 84. Meanwhile, main body control device 84 outputs a driving signal even to third control device 83 at the same timing as the driving signal outputted to first control device 81, and third control device 83 outputs an external synchronization signal to imaging device 72 based on the driving signal. Therefore, the image of wafer W may be picked up.

The controls may be executed according to, for example, a computer program recorded in main body control device 84 or computer programs recorded in various storage media which are readable by main body control device 84.

Next, referring to FIG. 11, a substrate processing method according to another exemplary embodiment will be described.

Figure 11:
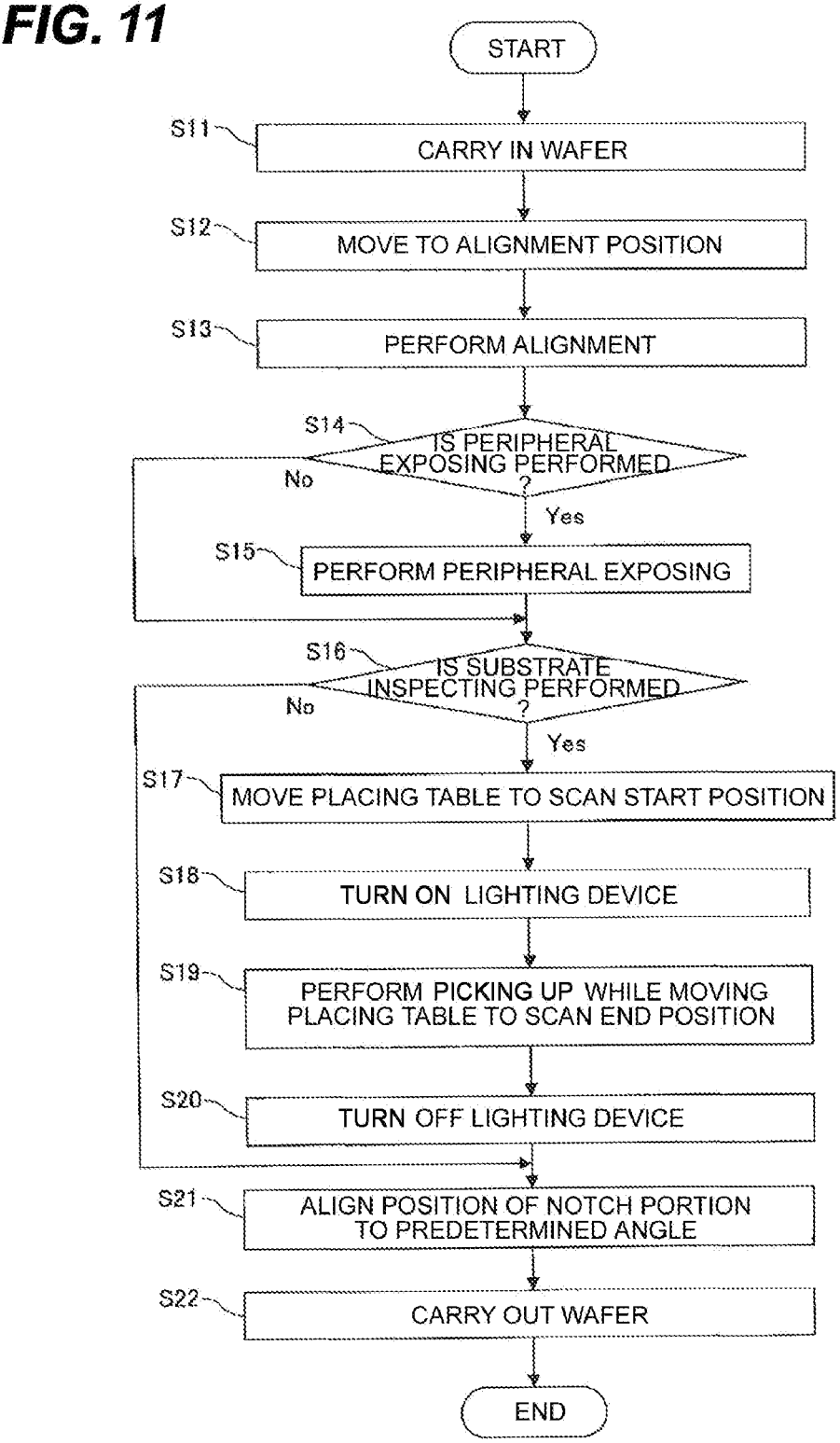
FIG. 11 is a flowchart illustrating a sequence of respective processes in a substrate processing method according to another exemplary embodiment of the present disclosure.

FIG. 11 is a flowchart illustrating a sequence of respective processes in a substrate processing method according to the present exemplary embodiment.

A program for executing a resist forming method including a substrate processing method is recorded in advance in main body control device 84 as a process recipe. Based on the process recipe recorded in main body control device 84, the following processing is executed.

Substrate processing having three patterns including a case where both peripheral exposing process and substrate inspecting process are performed as the processing recipe (recipe 1), a case where only the peripheral exposing process is performed without the substrate inspecting process as the processing recipe (recipe 2), and a case where only the substrate inspecting process is performed without the peripheral exposing process as the processing recipe (recipe 3) will be described.

When any one of processing recipes 1 to 3, that is, processing including at least one of the peripheral exposing process and the substrate inspecting process of wafer W is performed, wafer W is carried in first from transport hole 44 by transport arm A3 to be disposed on placing table 33 (step S11). In this case, placing table 33 stands by at a wafer carry-in/out position P1 (a position marked with dotted line in FIG. 5) at the other end side in casing 31 in advance.

Subsequently, placing table 33 is moved to alignment position P2 (a position marked with a solid line in FIG. 5) at one end side of casing 31 by movement driving unit 35 (step S12).

Subsequently, a notch portion of wafer W is detected by sensor unit 41, wafer W is rotated based on the position of the notch portion, and the position of notch portion of wafer W is aligned to be a predetermined angular position (step S13). The predetermined angular position is selected as a predetermined angular position according to for example, each recipe described above and a more detailed processing condition.

Subsequently, it is determined whether the peripheral exposing process is performed (step S14). When the recipe number is recipe 1 or recipe 2, the peripheral exposing process is performed (step S15). Meanwhile, when the recipe number is recipe 3, the peripheral exposing process (step S15) is skipped and step S16 is performed.

In the peripheral exposing process (step S15), light B from light source 54 is emitted from emission-side slit 61 formed in irradiating unit 53 and evenly irradiated to a predetermined area A of a peripheral portion on the surface of wafer W having the resist film R. In this state, wafer W is rotated by rotation driving unit 34, and as a result, light B is irradiated to redundant resist film RA of the peripheral portion of the surface of wafer W to achieve the peripheral exposing process.

Subsequently, it is determined whether the substrate inspecting process is performed (step S16). When the recipe number is recipe 1 or recipe 3, the substrate inspecting process is performed (steps S17 to S20). Meanwhile, when the recipe number is recipe 2, the substrate inspecting process (steps S17 to S20) are skipped and step S21 is performed.

In the substrate inspecting process (steps S17 to S20), placing table 33 is moved to a scan start position for picking up the image of wafer W using motor 39 (step S17). When alignment position P2 and the scan start position are the same as each other, placing table 33 may not be moved.

Subsequently, lighting device 74 is turned ON (step S18). As shown in FIG. 5, when the light source of lighting device 74 is the same as light source 54 of peripheral exposing unit 50, and light from light emitting unit 51 is branched from light guiding member 52 by light guiding member 52a to be guided to lighting device 74, a shutter (not shown) may be opened.

Subsequently, when wafer W passes below half mirror 73 while placing table 33 is moved up to wafer carry-in/out position P1 which is a scan end position at a predetermined speed by motor 39, the surface of wafer W is picked up by imaging device 72 (step S19). Placing table 33 stops at wafer carry-in/out position P1.

Subsequently, lighting device 74 is turned OFF (step S20). As shown in FIG. 5, when the light source of lighting device 74 is the same as light source 54 of peripheral exposing unit 50 and the light from light emitting unit 51 is branched from light guiding member 52 by light guiding member 52a to be guided to lighting device 74, the shutter (not shown) may be closed.

Subsequently, at the scan end position (wafer carry-in/out position P1), the position of the notch portion of wafer W is aligned with a predetermined angular position by rotation driving unit 34 (step S21).

Wafer W is then carried out from transport hole 44 by transport arm A3 (step S22), thereby completing the substrate processing according to recipes 1 to 3.

Next, in the substrate processing, dealing with an error which occurs at any one portion of substrate processing apparatus 30 will be described.

Table 1 shows a dealing method when the error occurs at any one portion of substrate processing apparatus 30 when each substrate processing is performed according to recipes 1 to 3.

TABLE 1

| | | Parts where error occurs | | |
|---|---|---|---|---|
| Recipe No. | Content of recipe | Peripheral exposing unit | Substrate inspecting unit | Transport unit or alignment unit |
| 1 | Peripheral exposing process and Substrate inspecting process | Stop Alarm outputted | Only substrate inspecting process skipped and continued Warning alarm outputted | Stop Alarm outputted |
| 2 | Only peripheral exposing process | Stop Alarm outputted | Continued Warning alarm outputted | Stop Alarm outputted |
| 3 | Only substrate inspecting process | Continuously processed Warning alarm outputted | Stop Alarm outputted | Stop Alarm outputted |

Table 2 shows an error type and an error detecting method at each portion where the error occurs when the error occurs in peripheral exposing unit 50.

TABLE 2

| Parts where error occurs | Light source | Exposing unit | Shutter |
|---|---|---|---|
| Error type | Lighting incapability | Excessive temperature rise state | Opening/closing operation incapability |
| Error detection method | Electrical circuit | Temperature fuse | Light amount sensor |

First, as shown in Table 1, if the substrate processing is performed according to recipe 1 or 2 when the error occurs in peripheral exposing unit 50, the substrate processing itself stops and an alarm indicating occurrence of the error and stoppage is outputted. If the substrate processing is performed according to recipe 3 when the error occurs in peripheral exposing unit 50, the substrate processing itself does not stop and the substrate inspecting process is continuously performed by substrate inspecting unit 70 and a warning alarm warning the occurrence of the error is outputted. That is, in the present exemplary embodiment, when the error occurs in peripheral exposing unit 50, if the peripheral exposing process is not included in predetermined substrate processing, the substrate processing is continuously performed, if the peripheral exposing process is included in the predetermined substrate processing, the substrate processing stops.

The reason is that an error may occur on the processed wafer when the peripheral exposing process is performed while the error occurs in peripheral exposing unit 50 because peripheral exposing unit 50 is a process module that actually executes a process with respect to wafer W. Therefore, if the peripheral exposing process is not included in the predetermined substrate processing, the substrate processing may be continuously performed, but if the peripheral exposing process is included in the predetermined substrate processing, the substrate processing cannot be continuously performed.

Examples in which the error occurs in peripheral exposing unit 50 include, as shown in Table 2, a case where light source 54 is incapable of lighting, a case where light emitting unit 51 is in an excessive temperature rise state, and a case where shutter 62 is incapable of opening/closing. The case where light source 54 is incapable of lighting may be detected by, for example, electrical circuit 54a of light source 54. The case where light emitting unit 51 is in the excessive temperature rise state may be detected by temperature fuse 56a installed around light emitting unit 51. The case where shutter 62 is incapable of opening/closing may be detected by light amount sensor 64 installed in casing 31.

As shown in Table 1, when the substrate processing is performed according to recipe 1 and the error occurs in substrate inspecting unit 70, only the substrate inspecting process is skipped, the peripheral exposing process of the substrate processing is continuously performed, and the warning alarm warning the occurrence of the error is outputted. When the substrate processing is performed according to recipe 2 and the error occurs in substrate inspecting unit 70, the substrate processing itself does not stop and the substrate processing is continuously performed and the warning alarm warning the occurrence of the error is outputted. When the substrate processing is performed according to recipe 3 and the error occurs in substrate inspecting unit 70, the substrate inspecting process is not performed and the substrate is transported to a next module to output an alarm notifying the occurrence of the error and stoppage. That is, in the present exemplary embodiment, when the error occurs in substrate inspecting unit 70, in the case where the substrate inspecting process is included in the predetermined substrate processing, the substrate inspecting process is skipped and the substrate is transported to a processing module performing postprocessing.

The reason is that there is no possibility that the error may occur on the processed wafer even when the peripheral exposing process is performed while the error occurs in the substrate inspecting unit 70 because substrate inspecting unit 70 is not the process module that actually executes the process with respect to wafer W. Therefore, when the peripheral exposing process is included in the predetermined substrate processing, the substrate inspecting process is skipped, and thereafter, the peripheral exposing process may be continuously performed.

An example in which the error occurs in substrate inspecting unit 70 may include a case where a communication error occurs between imaging device 72 and image processing unit 83a of third control device 83.

As shown in Table 1, when the error occurs in transport unit 32 or alignment unit 40, the substrate processing itself stops and the alarm notifying the occurrence of the error and the stoppage is outputted even though the substrate processing is performed according to any one of recipes 1 to 3. The reason is that both of the peripheral exposing process and the substrate inspecting process cannot be performed from the first because the wafer cannot be transported to an appropriate position when the error occurs in transport unit 32 or alignment unit 40.

According to the present exemplary embodiment, in the substrate processing apparatus for performing the predetermined substrate processing including at least one of the peripheral exposing process and the substrate inspecting process, when the peripheral exposing process is not included in the predetermined substrate processing and the error occurs in the peripheral exposing unit, the predetermined substrate processing is continuously performed. When the substrate inspecting process is included in the predetermined substrate processing and the error occurs in the substrate inspecting unit, the substrate inspecting process is skipped. Therefore, a work load of a substrate transporting device can be reduced, an installation area of an entire processing system can be reduced, and substrate processing can be prevented from stopping when an error occurs in a part used for only any one of peripheral exposing process and substrate inspecting process.

In the exemplary embodiments as described above, even though the semiconductor wafer is used as a substrate to be processed, other substrate such as, for example, a glass substrate for flat panel display may be applied for the present disclosure.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A substrate processing apparatus comprising:
    a transport device including a substrate holder configured to hold the substrate, a rotation driver configured to rotate the substrate holder about the center of the substrate holder as a rotational axis, and a movement driver configured to move the substrate holder horizontally;
    a peripheral exposing device including an irradiation device that irradiates light and configured to perform a peripheral exposing process that exposes a peripheral portion of the substrate by irradiating the light to the peripheral portion of the substrate using the irradiation device while rotating the substrate held by the substrate holder using the rotation driver;
    a substrate inspecting device including an image pick up device that picks up an image and configured to perform a substrate inspecting process that inspects the substrate based on the picked up image while moving the substrate held by the substrate holder using the movement driver; and
    a controller configured to control the substrate processing apparatus including the transport device, the peripheral exposing device, and the substrate inspecting device,
    wherein the controller is programmed to control the transport device, the peripheral exposing device and the substrate inspecting device in order to perform a predetermined substrate processing including either one of the peripheral exposing process and the substrate inspecting process or both,
    when it is determined by the controller that an error occurs in the peripheral exposing device and the predetermined substrate processing includes the peripheral exposing process, the controller controls the transport device, the peripheral exposing device and the substrate inspecting device such that the predetermined substrate processing is stopped, and
    when it is determined by the controller that an error occurs in the substrate inspecting device and the predetermined substrate processing includes the substrate inspecting process while no error occurs in both of the transport device and the peripheral exposing device, the controller controls the transport device, the peripheral exposing device and the substrate inspecting device such that the substrate inspecting process is skipped while the peripheral exposing process continues.

2. The substrate processing apparatus of claim 1, wherein the peripheral exposing device includes a light emitting device configured to emit the light to be irradiated by the irradiation device, and
    the controller controls the transport device, the peripheral exposing device and the substrate inspecting device such that the predetermined substrate processing is stopped when the peripheral exposing process is included in the predetermined substrate processing and an error occurs in the light emitting device.

3. The substrate processing apparatus of claim 1, wherein the controller controls the transport device, the peripheral exposing device and the substrate inspecting device such that the predetermined substrate processing is stopped when the peripheral exposing process is included in the predetermined substrate processing and the peripheral exposing device is in a state where temperature is rising.

4. The substrate processing apparatus of claim 1, wherein the peripheral exposing device includes a shutter configured to transmit/interrupt the light to be irradiated by the irradiation device, and the control unit controls the transport device, the peripheral exposing device and the substrate inspecting device such that the predetermined substrate processing is stopped when the peripheral exposing process is included in the predetermined substrate processing and an error occurs in the shutter.

5. The substrate processing apparatus of claim 1, wherein the substrate inspecting device includes an image processor configured to process an image picked up by the image pick up device, and the controller controls the transport device, the peripheral exposing device and the substrate inspecting device such that the substrate inspecting process is skipped when no error occurs in both of the peripheral exposing device and the transport device, the substrate inspecting process is included in the predetermined substrate processing, and a communication error occurs between the image pick up device and the image processor.

6. The substrate processing apparatus of claim 1, wherein the transport device includes an alignment device configured to align a rotation angular position of the substrate held by the substrate holder.

7. A substrate processing method for performing a predetermined substrate processing using a substrate processing apparatus including a transport device, a peripheral exposing device, a substrate inspecting device, and a controller, the method comprising:

exposing a peripheral portion of a substrate by irradiating light to the peripheral portion of the substrate using an irradiation device included in the peripheral exposing device while rotating the substrate held by a substrate holder included in the transport device about the center of the substrate holder as a rotational axis;

picking up an image of the substrate using an image pick up device included in the substrate inspecting device and inspecting the substrate based on the picked up image while moving the substrate held by the substrate holder horizontally;

performing a predetermined substrate processing including either one of the peripheral exposing process and the substrate inspecting process or both by controlling the transport device, the peripheral exposing device and the substrate inspecting device;

when it is determined by the controller that an error occurs in the peripheral exposing device and the predetermined substrate processing includes the peripheral exposing process, stopping the predetermined substrate processing; and when it is determined by the controller that an error occurs in the substrate inspecting device and the predetermined substrate processing includes the substrate inspecting process while no error occurs in both of the transport device and the peripheral exposing device, skipping the picking up and the inspecting while continuing the peripheral exposing process.

8. The substrate processing method of claim 7, wherein the peripheral exposing device includes a light emitting device configured to emit the light to be irradiated by the irradiation device, and the method further comprising stopping the predetermined substrate processing when the exposing is included in the predetermined substrate processing and an error occurs in the light emitting device.

9. The substrate processing method of claim 7, further comprising stopping the predetermined substrate processing when the exposing is included in the predetermined substrate processing and the peripheral exposing device is in a state where temperature is rising.

10. The substrate processing method of claim 7, wherein the peripheral exposing device includes a shutter configured to transmit/interrupt the light to be irradiated by the irradiation device, and the method further comprising stopping the predetermined substrate processing when the exposing is included in the predetermined substrate processing and an error occurs in the shutter.

11. The substrate processing method of claim 7, wherein the substrate inspecting device includes an image processor configured to process the image picked up by the image pick up device, and the method further comprising skipping the picking up and the inspecting when no error occurs in both of the peripheral exposing device and the transport device, the picking up and the inspecting are included in the predetermined substrate processing, and a communication error occurs between the image pick up device and the image processor.

12. The substrate processing method of claim 7, wherein an alignment process of aligning a rotation angular position of the substrate held by the substrate holder is performed before the predetermined substrate processing is performed.

13. A non-transitory computer readable recording medium storing a computer executable program that, when executed, causes a computer to perform the substrate processing method of claim 7.

* * * * *